(12) United States Patent
Argudayev et al.

(10) Patent No.: US 8,652,552 B2
(45) Date of Patent: Feb. 18, 2014

(54) APPARATUS AND A METHOD FOR ESTIMATING THE AIR HUMIDITY WITHIN AN OVEN CAVITY

(75) Inventors: Sergey Argudayev, St. Petersburg (RU); Vladimir Gerasimov, St. Petersburg (RU); Roberto Giordano, Pozzuolo del Fruili (IT)

(73) Assignee: Electrolux Home Products Corporation N.V., Brussels (BE)

( * ) Notice: Subject to any disclaimer, the term of this patent is extended or adjusted under 35 U.S.C. 154(b) by 356 days.

(21) Appl. No.: 13/147,435

(22) PCT Filed: Feb. 18, 2010

(86) PCT No.: PCT/EP2010/001004
§ 371 (c)(1),
(2), (4) Date: Aug. 2, 2011

(87) PCT Pub. No.: WO2010/094473
PCT Pub. Date: Aug. 26, 2010

(65) Prior Publication Data
US 2012/0225179 A1  Sep. 6, 2012

(30) Foreign Application Priority Data
Feb. 19, 2009 (EP) .................................... 09002306

(51) Int. Cl.
*G01N 29/024* (2006.01)
*A23L 1/01* (2006.01)

(52) U.S. Cl.
USPC .................. 426/231; 73/24.04; 73/861.27

(58) Field of Classification Search
CPC ............................. A23L 1/01; G01N 29/024
USPC ............ 426/523, 231; 73/24.04, 861.27, 73/861.29, 861.22, 861.25, 861.26; 99/468
See application file for complete search history.

(56) References Cited

U.S. PATENT DOCUMENTS 5,365,039 A * 11/1994 Chaudoir ...................... 219/401
5,689,060 A   11/1997 Matsushima
(Continued)

FOREIGN PATENT DOCUMENTS

| DE | 19841154 | 4/2000 |
| DE | 10143841 | 4/2003 |
| EP | 0174627  | 3/1986 |

OTHER PUBLICATIONS

International Search Report for PCT/EP2010/001004, dated Apr. 29, 2010, 2 pages.

*Primary Examiner* — Steven Leff
(74) *Attorney, Agent, or Firm* — Pearne & Gordon LLP

(57) ABSTRACT

The present invention relates to an apparatus for estimating the air humidity within an oven cavity (14) by using ultrasound waves with at least two different frequencies ($f_1$, $f_2$). Said apparatus comprises at least one ultrasound transmitter (10) for generating the ultrasound waves, at least one ultrasound receiver (12) for receiving the ultrasound waves and at least one phase detecting device for detecting the phase ($\varphi_1$, $\varphi_2$) of the ultrasound wave at the ultrasound receiver (12) relative to the same ultrasound wave with the same frequency ($f_1$, $f_2$) at the ultrasound transmitter (10). Said apparatus comprises further at least one evaluation unit for calculating the velocity (V) of the ultrasound waves on the basis of the phases ($\varphi_1$, $\varphi_2$) and frequencies ($f_1$, $f_2$) of the ultrasound waves with the two different frequencies ($f_1$, $f_2$), at least one temperature sensor (32) for detecting the temperature (T) in the oven cavity (14) and at least one estimation unit for estimating the humidity in the oven cavity (14) on the basis of the temperature (T) and the velocity (V) of the ultrasound waves. Further, the present invention relates to a corresponding method for estimating the air humidity within an oven cavity (14).

14 Claims, 3 Drawing Sheets

(56) References Cited

U.S. PATENT DOCUMENTS

| | | | |
|---|---|---|---|
| 6,178,827 B1 * | 1/2001 | Feller | 73/861.27 |
| 6,370,963 B1 * | 4/2002 | Feller | 73/861.29 |
| 6,422,093 B2 * | 7/2002 | Feller | 73/861.27 |
| 6,575,044 B1 * | 6/2003 | Feller | 73/861.27 |
| 7,093,502 B2 * | 8/2006 | Kupnik et al. | 73/861.29 |
| 2006/0207329 A1 * | 9/2006 | Page et al. | 73/597 |
| 2008/0223147 A1 * | 9/2008 | Deutscher et al. | 73/861.27 |

* cited by examiner

APPARATUS AND A METHOD FOR ESTIMATING THE AIR HUMIDITY WITHIN AN OVEN CAVITY

The present invention relates to an apparatus for estimating the air humidity within an oven cavity according to claim 1. Further the present invention relates to a method for estimating the air humidity within an oven cavity according to claim 7. In particular, the present invention relates to an apparatus and a method for estimating the air humidity within the oven cavity of an electric oven.

During a cooking process the temperature within the oven cavity is the most important parameter. Another important parameter is the humidity of the air within the oven cavity. An ordinary humidity sensor is appropriate only for temperatures up to 200° C. However, in conventional ovens the temperature during the cooking process may be 250° C. During a pyrolytic cleaning the temperature may be even higher.

Another method for estimating the humidity within a space is the detection of the velocity of sound or ultrasound through this space. The velocity of sound and ultrasound depends on the humidity and temperature, but not on the ambient pressure. Since the temperature in the oven cavity is known, the humidity can be determined by the velocity of the sound or ultrasound.

The document U.S. Pat. No. 5,689,060 discloses a humidity measuring device for a heat cooker. The phase difference between received sonic waves through reference air and through tested air is measured. However, the phase difference may not exceed ¼ of the wavelength. Thus, the frequency of the sonic wave must be about 4 kHz. The sonic wave with the frequency of 4 kHz is audible, so that the user hears the sound.

In the document EP 0 174 627 B1 a gas concentration measuring instrument using ultrasound waves is disclosed. In particular, the gas concentration measuring instrument is provided for measuring the concentration of carbon dioxide. The measuring instrument comprises an ultrasound transmitter and receiver. However, this measuring instrument is not suitable for high temperatures.

The document DE 101 43 841 A1 discloses a cooking oven with a device for detecting the humidity. Said device comprises a sound or ultrasound transmitter, a sound or ultrasound receiver, a temperature sensor and means for measuring the runtime of the sound or ultrasound waves. On the basis of the runtime the velocity of the sound or ultrasound waves can be calculated. The humidity can be estimated from the temperature and the velocity of the sound or ultrasound waves.

It is an object of the present invention to provide an apparatus and a method for estimating the air humidity within an oven cavity with an improved accuracy, wherein the complexity of said apparatus and method is relative low.

This object of the present invention is achieved by the apparatus according to claim 1.

According to the present invention the apparatus for estimating the air humidity within an oven cavity by using ultrasound waves with at least two different frequencies comprises:
- at least one ultrasound transmitter for generating the ultrasound waves,
- at least one ultrasound receiver for receiving the ultrasound waves,
- at least one phase detecting device for detecting the phase of the ultrasound wave at the ultrasound receiver relative to the same ultrasound wave with the same frequency at the ultrasound transmitter,
- at least one evaluation unit for calculating the velocity of the ultrasound waves on the basis of the phases and frequencies of the ultrasound waves with the two different frequencies,
- at least one temperature sensor for detecting the temperature in the oven cavity, and
- at least one estimation unit for estimating the humidity in the oven cavity on the basis of the temperature in the oven cavity and the velocity of the ultrasound waves.

The main idea of the present invention is the use of two different frequencies. This allows the calculation of the velocity of the ultrasound waves by the two frequencies and the two corresponding phases. The humidity can be estimated on the basis of the velocity and the temperature. The maximum error of the estimated specific humidity is about 9%.

In a preferred embodiment of the present invention the ultrasound transmitter and/or the ultrasound receiver are arranged at or within opposite walls of the oven cavity. This allows a distance between ultrasound transmitter and the ultrasound receiver, which is as big as possible.

In particular, the ultrasound transmitter and/or the ultrasound receiver are arranged in front or rear portions of side walls of the oven cavity. In those positions there is always a direct connection between the ultrasound transmitter and the ultrasound receiver.

Further, the temperature sensor may be arranged between the ultrasound transmitter and the ultrasound receiver. Thus, the temperature and the velocity of the ultrasound waves relates to the same region.

Preferably, the evaluation unit is provided for calculating the velocity on the basis of the distance between the ultrasound transmitter and the ultrasound receiver. The distance between the ultrasound transmitter and the ultrasound receiver is a given size and need not to be measured.

According to the preferred embodiment of the present invention the apparatus is provided for an electric oven.

The object of the present invention is further achieved by the method according to claim 7.

According to the present invention the method for estimating the air humidity within an oven cavity comprises the steps of:
- generating ultrasound waves with at least two different frequencies,
- receiving the ultrasound waves with the at least two different frequencies,
- detecting the phase of the ultrasound wave with a first frequency at the ultrasound receiver relative to the same ultrasound wave with the first frequency at the ultrasound transmitter,
- detecting the phase of the ultrasound wave with a second frequency at the ultrasound receiver relative to the same ultrasound wave with the second frequency at the ultrasound transmitter,
- calculating the velocity of the ultrasound waves on the basis of the phases and frequencies of the ultrasound waves with the two different frequencies,
- detecting the temperature within the oven cavity, and
- estimating the humidity in the oven cavity on the basis of the temperature and the velocity of the ultrasound waves.

The main idea of the present invention is the use of two different frequencies. This allows the calculation of the velocity of the ultrasound waves by the two frequencies and the two corresponding phases. The humidity can be estimated on the basis of the velocity and the temperature. The maximum error of the estimated specific humidity is about 9%.

In a preferred embodiment of the present invention a first frequency is marginally bigger and a second frequency is marginally smaller than a resonance frequency of an ultrasound transducer formed by the ultrasound transmitter and the ultrasound receiver. This is a contribution to the accuracy of the inventive method.

Further, the velocity of the ultrasound waves may be estimated by the distance between the ultrasound transmitter and the ultrasound receiver. The distance between the ultrasound transmitter and the ultrasound receiver is a given size and need not to be measured.

In particular, the velocity of the ultrasound waves is estimated by $V=[2\pi \cdot L \cdot (f_1-f_2)]/\Delta\phi$, wherein $\Delta\phi=\phi_1-\phi_2$, if $\phi_1>\phi_2$, and $\Delta\phi=\phi_1-\phi_2+2\pi$, if $\phi_1<\phi_2$. Thus, the value of $\Delta\phi$ is positive in any case. The above-mentioned formula is valid, if $L<[V_{min}/(f_1-f_2+\Delta(\Delta\phi))-\Delta L]$, wherein $V_{min}=331$ m/s is the minimal possible sound speed, $\Delta(\Delta f)$ is the possible variation of $f_1-f_2$ and $\Delta L$ is the possible variation of L. Further $f_1$ is the first frequency, $f_2$ is the second frequency, $\phi_1$ is the phase corresponding with the first frequency $f_1$, $\phi_2$ is the phase corresponding with the second frequency $f_2$ and L is the distance between the ultrasound transmitter and the ultrasound receiver.

Preferably, the temperature is detected within a space between the ultrasound transmitter and the ultrasound receiver. Thus, the measured temperature and the calculated velocity of the ultrasound waves relate to the same region.

For example, the frequencies are generated by dividing a predetermined clock frequency. In particular, the frequencies are generated by a common generator.

The estimated humidity may be used for a cooking program in order to optimize the cooking process.

At last, a computer program product is provided. Said computer program product is stored on a computer usable medium, comprising computer readable program means for causing a computer to perform the method described above.

The novel and inventive features believed to be the characteristic of the present invention are set forth in the appended claims.

The invention will be described in further detail with reference to the accompanied drawings, in which FIG. 1 illustrates a schematic diagram of a frequency spectrum of an ultrasound transducer according to a preferred embodiment of the present invention;

Figure 1:
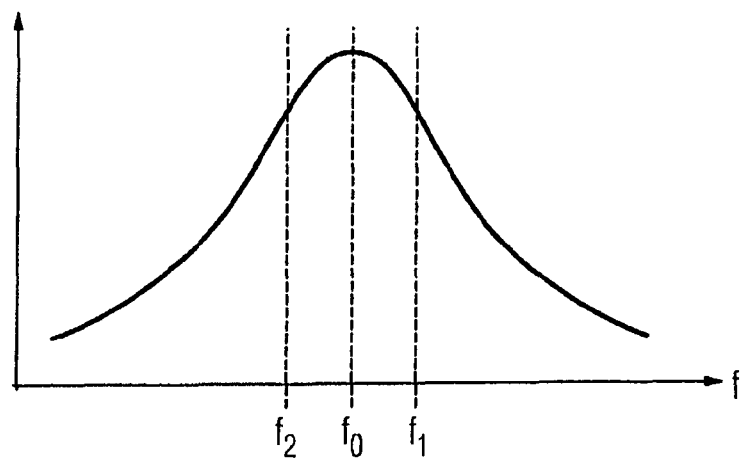

FIG. 1 illustrates a schematic diagram of a frequency spectrum of an ultrasound transducer according to a preferred embodiment of the present invention. The frequency spectrum comprises a peak at a resonance frequency $f_0$. A first frequency $f_1$ and a second frequency $f_2$ are provided for measuring the velocity of the ultrasound waves. The first frequency $f_1$ and the second frequency $f_2$ surround the resonance frequency $f_0$. The first frequency $f_1$ is marginally bigger than the resonance frequency $f_0$. The second frequency $f_2$ is marginally smaller than the resonance frequency $f_0$.

Figure 2:
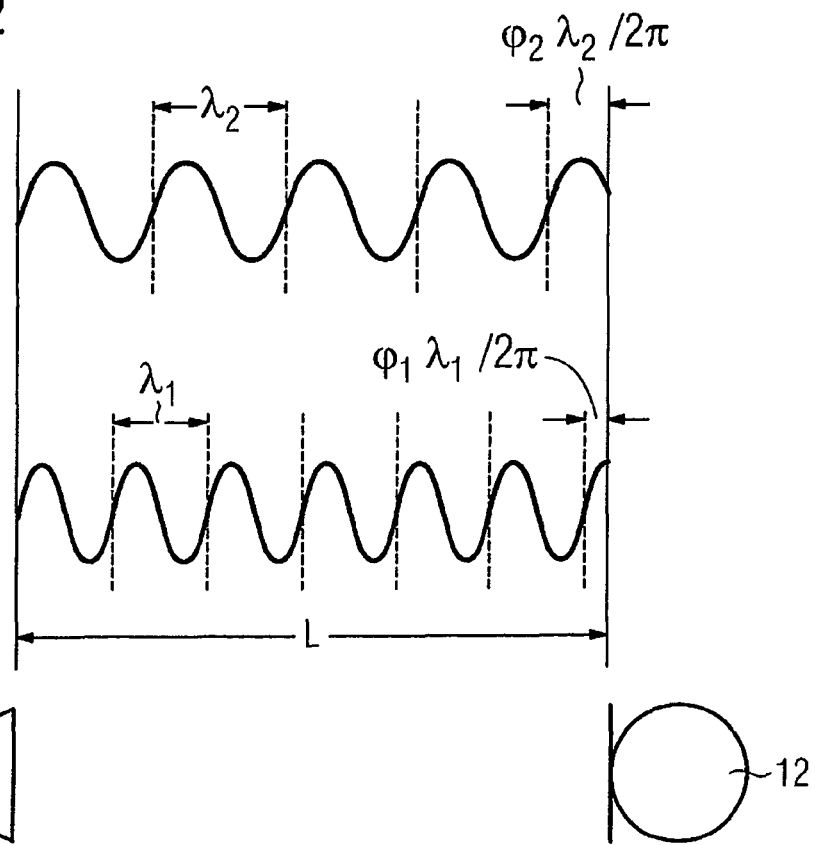
FIG. 2 illustrates a schematic diagram of two ultrasound waves with different wavelengths between an ultrasound transmitter and an ultrasound receiver according to the preferred embodiment of the present invention.

FIG. 2 illustrates a schematic diagram of two ultrasound waves with different wavelengths $\lambda_1$ and $\lambda_2$ between an ultrasound transmitter 10 and an ultrasound receiver 12 according to the preferred embodiment of the present invention. The ultrasound transmitter 10 and the ultrasound receiver 12 form the ultrasound transducer.

The first ultrasound wave has the first frequency $f_1$ and the first wavelength $\lambda_1$. The second ultrasound wave has the second frequency $f_2$ and the second wavelength $\lambda_2$. Between the ultrasound transmitter 10 and the ultrasound receiver 12 is the distance L.

The relationship between the distance L and the first wavelength $\lambda_1$ is given by $$L = n_1 \cdot \lambda_1 + \phi_1 \cdot \lambda_1/(2\pi),$$

wherein $n_1$ is the number of the complete first wavelengths $\lambda_1$ within the distance L and $\phi_1$ is the phase of the first ultrasound wave at the ultrasound receiver 12 relative to the first ultrasound wave at the ultrasound transmitter 10.

In a similar way, the relationship between the distance L and the second wavelength $\lambda_2$ is given by $$L = n_2 \cdot \lambda_2 + \phi_2 \cdot \lambda_2/(2\pi),$$

wherein $n_2$ is the number of the complete second wavelengths $\lambda_2$ within the distance L and $\phi_2$ is the phase of the second ultrasound wave at the ultrasound receiver 12 relative to the second ultrasound wave at the ultrasound transmitter 10.

The first frequency $f_1$ and the second frequency $f_2$ may be generated by a common frequency generator with a given clock frequency $f_C$. The first frequency $f_1$ and the second frequency $f_2$ are obtained by division of the clock frequency $f_C$ by a divisor $N_1$ and $N_2$, respectively:

$$f_1 = f_C/N_1, f_2 = f_C/N_2.$$

The resulting velocity of the ultrasound waves is given by $$V = (2\pi \cdot L \cdot \Delta f)/\Delta\phi,$$

wherein the frequency difference $$\Delta f = f_1 - f_2 = f_C/N_1 - f_C/N_2 > 0$$

must be positive and the side condition $$L < V_{min}/[\Delta f + \Delta(\Delta f)] - \Delta L$$

must be satisfied. If said side condition is satisfied, then the phases $\phi_1$ and $\phi_2$ are never equal to each other. Thus, the value of $\Delta\phi$ is always positive. Thereby L is the distance between the ultrasound transmitter 10 and the ultrasound receiver 12, $\Delta L$ is the variation range of L, $\Delta\phi$ is the phase difference, $V_{min}$ is the minimal possible velocity of the ultrasound waves and $\Delta(\Delta f)$ is the variation range of the frequency difference $\Delta f$.

If $\phi_1 \geq \phi_2$, then the phase difference $\Delta\phi$ is given by $\Delta\phi=\phi_1-\phi_2$. Else, if $\phi_1<\phi_2$, then the phase difference $\Delta\phi$ is given by $\Delta\phi=\Delta_1-\phi_2+2\pi$. The variation range $\Delta(\Delta f)$ of the frequency difference $\Delta f$ is given by $$\Delta(\Delta f) = f_C \cdot \delta f_C/N_1 - f_C \cdot \delta f_C/N_2,$$

wherein $\delta f_C$ is the relative error of the clock frequency $f_C$.

The minimal possible velocity $V_{min}$ of the ultrasound waves is $V_{min}=331.244$ m/s for dry air at a temperature of $T=0°$ C. and a pressure of $P=1$ atm.

By using realistic values, i.e. $f_C=20$ MHz, $\delta f_C=0.5\%$, $\Delta L=3$ mm, $N_1=497$ and $N_2=503$, the distance L between the ultrasound transmitter 10 and the ultrasound receiver 12 must be L<684 mm.

The velocity of the ultrasound waves depends on temperature and humidity by the expression:

$$V = \sqrt{\{[(7+X_V) \cdot Z \cdot R \cdot T]/[(5+X_V) \cdot M_A \cdot (1-X_V \cdot (1-M_V/M_A))]\}},$$

wherein T is the temperature, $M_A$ is the molar mass of dry air, $M_V$ is the molar mass of water vapour, R is the molar ideal gas constant and Z is the compressibility factor. The numerical values of the constants are given by $$M_A = 0.029 \text{ kg/mol},$$

$$M_V = 0.018 \text{ kg/mol},$$

$$R = 8.315 \text{ J/(mol·K)}.$$

The compressibility factor Z depends on the temperature T, the molar fraction $X_V$ and the pressure P. However, in this case the compressibility factor Z is about one.

The molar fraction $X_V$ of water vapour in the air is determined by the specific humidity SH $$X_V = (M_A \cdot SH)/[M_V + (M_A - M_V) \cdot SH].$$

The specific humidity SH is defined by $$SH = (m_V \cdot 100\%)/(m_A - m_V),$$

wherein $m_V$ is the weight of the water vapour part and $m_A$ is the weight of the dry air part. Said water vapour part and said dry air part form a real air-vapour mixture filling the same volume.

For realistic accuracies $\Delta V \pm 6.27$ m/s, $\Delta T \pm 5°$ C. and $\Delta P \pm 300$ mm/Hg, in the worst case the absolute error of the specific humidity is $\Delta SH \pm 9\%$.

If the specific humidity SH, the temperature T and the pressure P are known, then the relative humidity can be calculated $$RH = (P \cdot M_A \cdot SH \cdot 100\%)/\{P_{VS}(T) \cdot [M_V + (M_A - M_V) \cdot SH]\},$$

wherein $P_{VS}(T)$ is the saturation vapour pressure of water at a given temperature T.

Figure 3:
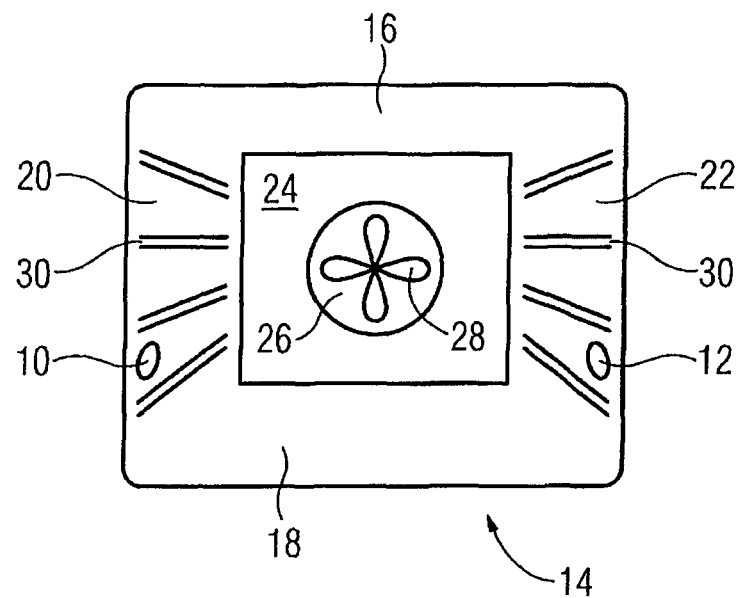
FIG. 3 illustrates a schematic diagram of a perspective front view of the inner space of an oven cavity according to a first embodiment of the present invention.

FIG. 3 illustrates a schematic diagram of a perspective front view of the inner space of an oven cavity 14 according to a first embodiment of the present invention. The oven cavity 14 is bordered by a top wall 16, a bottom wall 18, a left side wall 20, a right side wall 22 and a rear wall 24. The rear wall 24 includes a fan 26 comprising a propeller 28.

A number of side grids 30 are pair-wise arranged on the inner sides of the side walls 20 and 22. The side grids 30 of each pair are arranged at the same level. The side grids 30 extend horizontally along the inner sides of the side walls 20 and 22. The pair of side grids 30 is provided to support a tray or a grid.

In this embodiment the ultrasound transmitter 10 is arranged in a front portion of the left side wall 20. The ultrasound transmitter 10 is arranged between the two lowest side grids 30. In a similar way the ultrasound receiver 12 is arranged in a front portion of the right side wall 22 between the two lowest side grids 30, so that the ultrasound transmitter 10 and the ultrasound receiver 12 are ordered symmetrically.

The ultrasound transmitter 10 and the ultrasound receiver 12 are located in such positions, that the space between them is free from any matter. Thus, the propagation of the ultrasound waves from the ultrasound transmitter 10 and to the ultrasound receiver 12 is undisturbed. There is a direct geometric connection between the ultrasound transmitter 10 and the ultrasound receiver 12.

The distance L between the ultrasound transmitter 10 and the ultrasound receiver 12 is equal to the inner width of the oven cavity 14. A typical value of the inner width of the oven cavity 14 is L=440 mm. Said typical inner width of L=440 mm fortunately satisfies the above side condition L<684 mm.

Figure 4:
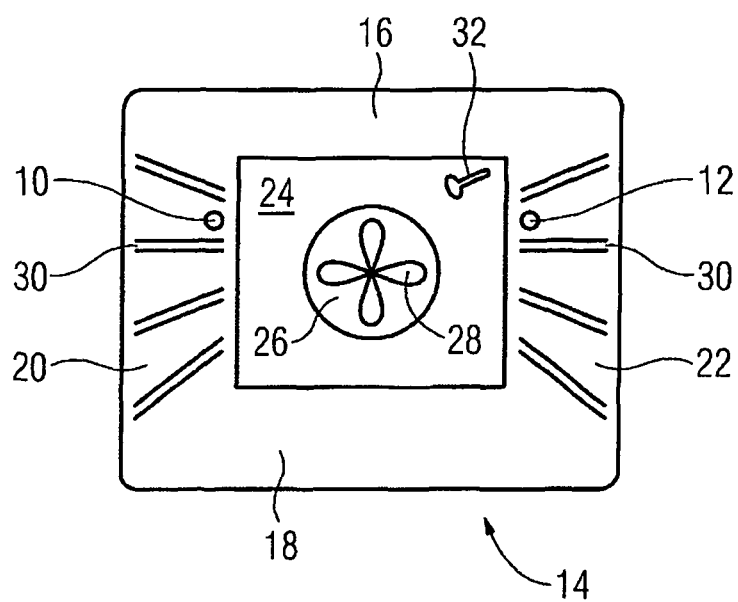
FIG. 4 illustrates a schematic diagram of a perspective front view of the inner space of the oven cavity according to a second embodiment of the present invention.

FIG. 4 illustrates a schematic diagram of a perspective front view of the inner space of the oven cavity 14 according to a second embodiment of the present invention. The oven cavity 14 is bordered by the top wall 16, the bottom wall 18, the left side wall 20, the right side wall 22 and the rear wall 24. The rear wall 24 includes the fan 26 with the propeller 28.

The number of side grids 30 is pair-wise arranged on the inner sides of the side walls 20 and 22. The side grids 30 of each pair are arranged at the same level. The side grids 30 extend horizontally along the inner sides of the side walls 20 and 22. The pair of side grids 30 is provided to support the tray or the grid.

In this embodiment the ultrasound transmitter 10 is arranged in a rear portion of the left side wall 20. The ultrasound transmitter 10 is arranged between the two upper side grids 30. In a similar way the ultrasound receiver 12 is arranged in a rear portion of the right side wall 22 between the two upper side grids 30, so that the ultrasound transmitter 10 and the ultrasound receiver 12 are ordered symmetrically.

Also in this embodiment the ultrasound transmitter 10 and the ultrasound receiver 12 are located in such positions, that the space between them is free from any matter. Thus, the propagation of the ultrasound waves from the ultrasound transmitter 10 and to the ultrasound receiver 12 is undisturbed. There is also a direct geometric connection between the ultrasound transmitter 10 and the ultrasound receiver 12.

A temperature sensor 32 is arranged at the rear wall 24. Said temperature sensor 32 is located in the region between the ultrasound transmitter 10 and the ultrasound receiver 12. Thus, the temperature can be detected in the same region, where the velocity of the ultrasound is estimated. Since the calculation of the humidity bases on the actual value of the temperature, the arrangement contributes to the accuracy of the calculation of the humidity.

Also in this embodiment the distance L between the ultrasound transmitter 10 and the ultrasound receiver 12 is equal to the inner width of the oven cavity 14. The typical value is L=440 mm, which fortunately satisfies the above side condition of L<684 mm.

Figure 5:
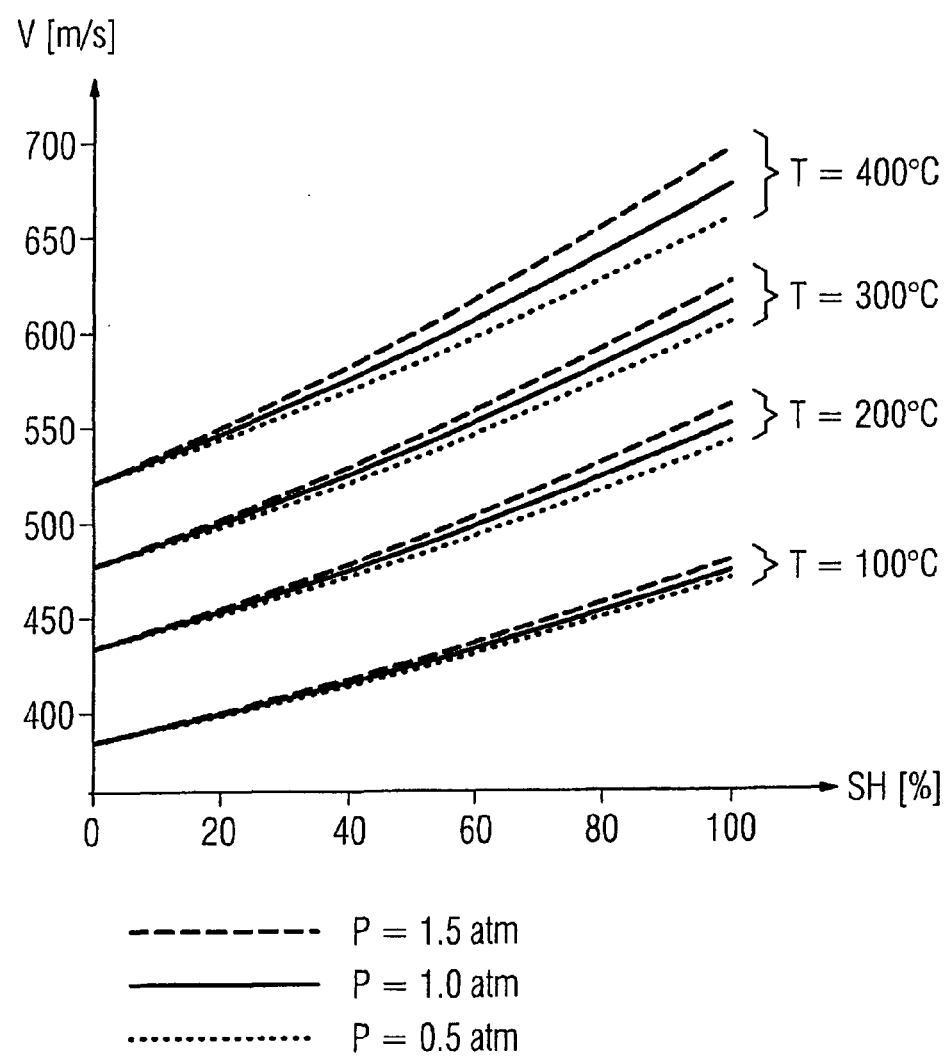
FIG. 5 illustrates a schematic diagram of the velocity of the ultrasound waves as a function of the specific humidity according to the preferred embodiment of the present invention.

FIG. 5 illustrates a schematic diagram of the velocity V of the ultrasound waves as a function of the specific humidity SH according to the preferred embodiment of the present invention.

The diagram shows twelve functions for three different pressures P=0.5 atm, P=1.0 atm and P=1.5 atm and four different temperatures T=100° C., T=200° C., T=300° C. and T=400° C. The pressure P=0.5 atm is represented by dotted lines, the pressure P=1.0 atm by solid lines and the pressure P=1.5 atm by dashed lines.

The velocity of the ultrasound wave increases marginally with a decreasing pressure for high humidity values. Further, the velocity of the ultrasound wave increases clearly with an increasing temperature for all humidity values.

With the function in FIG. 5 the humidity SH can be estimated accurately by the knowledge of the velocity V of the ultrasound waves and the temperature T within the oven cavity.

The accuracy for estimating the humidity can be improved by calibration on the basis of the above mentioned theoretical expressions. The calibration should be performed in the whole range of humidity between 0% and 100% for all possible temperatures up to 350° C. inside the oven. In particular, the calibration is advantageous, if the ultrasound waves do not form a narrow beam, so that the ultrasound waves may be reflected at the inner walls 16, 18, 20, 22 and 24 of the oven cavity 14. Then the ultrasound receiver 12 will receive the direct ultrasound waves from the ultrasound transmitter 10 as well as the reflected ultrasound waves. The reflected ultrasound waves may cause an error in the estimation of the velocity of the ultrasound waves. Said error may be compensated by the above calibration.

The present invention allows the estimation of the average humidity among the whole cavity, but not any localized humidity around a sensor. The present invention allows a very fast estimation of the humidity. Several repeated measurements and a subsequent calculation of an average value can improve the accuracy.

Appropriate ultrasound transmitters 10 and ultrasound receivers 12 with sufficient temperature and chemical resistance are available.

The ultrasound transmitter 10 and the ultrasound receiver 12 can be used for other purposes. For example, an open oven door may be detected. Further, it can be detected, if the oven cavity 14 is loaded or not.

The present invention can also be embedded in a computer program product, which comprises all the features enabling the implementation of the method described herein. Further, when loaded in a computer system, said computer program product is able to carry out these methods.

Although illustrative embodiments of the present invention have been described herein with reference to the accompanying drawing, it is to be understood that the present invention is not limited to those precise embodiments, and that various other changes and modifications may be affected therein by one skilled in the art without departing from the scope or spirit of the invention. All such changes and modifications are intended to be included within the scope of the invention as defined by the appended claims.

LIST OF REFERENCE NUMERALS 10 ultrasound transmitter
12 ultrasound receiver
14 oven cavity
16 top wall
18 bottom wall
20 left side wall
22 right side wall
24 rear wall
26 fan
28 propeller
30 side grid
32 temperature sensor
$f_0$ resonance frequency
$f_1$ first frequency
$f_2$ second frequency
$f_C$ clock frequency
$N_1$ divisor of the first frequency $f_1$
$N_2$ divisor of the second frequency $f_2$
$\Delta f$ difference frequency between $f_1$ and $f_2$
$\Delta(\Delta f)$ variation of the difference frequency $\Delta f$
$\lambda_1$ first wavelength
$\lambda_2$ second wavelength
L distance between transmitter 10 and receiver 12
$\Delta L$ variation of the distance L
$n_1$ number of complete first wavelengths $\lambda_1$
$n_2$ number of complete second wavelengths $\lambda_2$

The invention claimed is:

1. An apparatus for estimating the air humidity within an oven cavity (14) by using ultrasound waves with at least two different frequencies ($f_1$, $f_2$), wherein said apparatus comprises:

at least one ultrasound transmitter (10) for generating the ultrasound waves,
at least one ultrasound receiver (12) for receiving the ultrasound waves,
at least one phase detecting device for detecting the phase ($\phi_1, \phi_2$) of the ultrasound wave at the ultrasound receiver (12) relative to the same ultrasound wave with the same frequency ($f_1$, $f_2$), at the ultrasound transmitter (10),
at least one evaluation unit for calculating the velocity (V) of the ultrasound waves on the basis of the phases ($\phi_1, \phi_2$) and frequencies ($f_1$, $f_2$), of the ultrasound waves with the two different frequencies ($f_1$, $f_2$),
at least one temperature sensor (32) for detecting the temperature (T) in the oven cavity (14), and at least one estimation unit for estimating the humidity in the oven cavity (14) on the basis of the temperature (T) in the oven cavity (14) and the velocity (V) of the ultrasound waves.

2. The apparatus according to claim 1, characterized in, that the ultrasound transmitter (10) and/or the ultrasound receiver (12) are arranged at or within opposite walls (20, 22) of the oven cavity (14).

3. The apparatus according to claim 1, characterized in, that the ultrasound transmitter (10) and/or the ultrasound receiver (12) are arranged in front or rear portions of side walls (20, 22) of the oven cavity (14).

4. The apparatus according to claim 1, characterized in, that the temperature sensor (32) is arranged between the ultrasound transmitter (10) and the ultrasound receiver (12).

5. The apparatus according to claim 1, characterized in, that the evaluation unit is provided for calculating the velocity (V) on the basis of the distance (L) between the ultrasound transmitter (10) and the ultrasound receiver (12).

6. The apparatus according to claim 1, characterized in, that the apparatus is provided for an electric oven.

7. A method for estimating the air humidity within an oven cavity, wherein said method comprises the steps of:

generating ultrasound waves with at least two different frequencies ($f_1$, $f_2$),
receiving the ultrasound waves with the at least two different frequencies ($f_1$, $f_2$), detecting the phase ($\phi_1$) of the ultrasound wave with a first frequency ($f_1$) at the ultrasound receiver (12) relative to the same ultrasound wave with the first frequency ($f_1$) at the ultrasound transmitter (10),
detecting the phase ($\phi_2$) of the ultrasound wave with a second frequency ($f_2$) at the ultrasound receiver (12) relative to the same ultrasound wave with the second frequency ($f_2$) at the ultrasound transmitter (10),
calculating the velocity (V) of the ultrasound waves on the basis of the phases ($\phi_1, \phi_2$) and frequencies ($f_1$, $f_2$) of the ultrasound waves with the two different frequencies ($f_1$, $f_2$),
detecting the temperature (T) within the oven cavity (14), and
estimating the humidity in the oven cavity (14) on the basis of the temperature (T) and the velocity (V) of the ultrasound waves.

8. The method according to claim 7, characterized in, that a first frequency ($f_1$) is marginally bigger and a second frequency ($f_2$) is marginally smaller than a resonance frequency ($f_0$) of an ultrasound transducer formed by the ultrasound transmitter (10) and the ultrasound receiver (12).

9. The method according to claim 7, characterized in, that the velocity (V) of the ultrasound waves is estimated by the distance (L) between the ultrasound transmitter (10) and the ultrasound receiver (12).

10. The method according to claim 7, characterized in, that the velocity (V) of the ultrasound waves is estimated by $V=[2\pi \cdot L \cdot (f_1, f_2)]\Delta\phi$, wherein $\Delta\phi=\phi_1-\phi_2$, if $\phi_1>\phi_2$, and $\Delta\phi=\phi_1-\phi_2+2\pi$, if $\phi_1<\phi_2$, and wherein $f_1$ is the first frequency, $f_2$ is the second frequency, $\phi_2$ is the phase corresponding with the first frequency $f_1$, $\phi_2$ is the phase corresponding with the second frequency $f_2$ and L is the distance between the ultrasound transmitter (10) and the ultrasound receiver (12).

11. The method according to claim 7, characterized in, that the temperature (T) is detected within a space between the ultrasound transmitter (10) and the ultrasound receiver (12).

12. The method according to claim 7, characterized in, that the frequencies ($f_1$, $f_2$) are generated by dividing a predetermined clock frequency ($f_C$).

13. The method according to claim 7, characterized in, that the frequencies ($f_1$, $f_2$) are generated by a common generator.

14. The method according to claim 7, characterized in, that the estimated humidity is used for a cooking program in order to optimize the cooking process.

\* \* \* \* \*